(12) United States Patent
Wernet et al.

(10) Patent No.: US 6,852,534 B2
(45) Date of Patent: Feb. 8, 2005

(54) METHOD TO DETERMINE AN ENGRAFTING CELL DOSE OF HEMATOPOIETIC STEM CELL TRANSPLANT UNITS

(75) Inventors: Peter Wernet, Düsseldorf (DE); Gesine Kögler, Düsseldorf (DE); Johannes Fischer, Neuss (DE)

(73) Assignee: Kourion Therapeutics GmbH, Duesseldorf (DE)

( * ) Notice: Subject to any disclaimer, the term of this patent is extended or adjusted under 35 U.S.C. 154(b) by 55 days.

(21) Appl. No.: 09/985,334

(22) Filed: Nov. 2, 2001

(65) Prior Publication Data

US 2002/0094550 A1 Jul. 18, 2002

Related U.S. Application Data

(60) Provisional application No. 60/245,167, filed on Nov. 3, 2000.

(51) Int. Cl.[7] .................................................. C12N 5/08
(52) U.S. Cl. .............................. 435/372; 435/2; 435/4; 435/325; 424/93.7; 436/8; 600/368
(58) Field of Search ................................ 435/325, 4, 2, 435/372, 6; 424/93.7; 436/8; 600/368

(56) References Cited

PUBLICATIONS

Doerner et al., "Improved Automated Leucocyte Counting and Differential in Newborns Achieved by the Haematology Analyser Cell–Dyn 3500", XP–001058497, Clinical and Laboratory Haematology, Oxford, GB, vol. 17. No. 1, (Mar. 1995), pp. 23–30.

Walka et al., "Complete Blood Counts from Umbilical Cords of Healthy Term Newborns by Two Automated Cytometers", XP–001058402, ACTA Haematologica, vol. 100. No. 4. (1998), pp. 167–173.

Gluckman et al., "Hematopoietic Reconstitution in a Patient with Fanconi's Anemia by Means of Umbilical–Cord Blood from an HLA–Identical Sibling", New England Journal of Medicine (Oct. 1989), pp. 1174–1178.

Johannessen et al., "Automated Differential Leukocyte counts in newborn infants. Comparison of Coulter VCS and Technicon H1 with Manual Counts," Eur J. Haematol 1990, 45 suppl. 53, Chapter II, Comparison of Automated Haematology Analysers, pp. 41–44.

Kurtzberg et al., "Placental Blood as a Source of Hematopoietic Stem Cells for Transplantation into unrelated Recipients," New England Journal of Medicine, Partially HLA_ Mismatched Placental Blood as a Source of Hematopoietic Stem Cells, vol. 335, No. 3. (Jul. 1996), pp. 157–166.

Lim et al., "Influence of Delivery on Numbers of Leukocytes, Leukocyte Subpopulations, and Hematopoietic Progenitor Cells in Human Umbilical Cord Blood," Blood Cells (1994) Springer–Verlag, New York, Inc.20: pp. 547–559.

Rubinstein et al., "Outcomes Among 562 Recipients of Placental–Blood Transplants from Unrelated Donors," New England Journal of Medicine, vol. 339. No. 22, (Nov. 1998), pp. 1565–1577.

Rubinstein et al., "Processing and cryopreservation of placental/umbilical cord blood for unrelated bone marrow reconstitution", Proc. Natl. Acad. Sci USA, vol. 02, (Oct. 1995), pp. 10119–10122.

Johannes et al., Database Biosis "Online!Biosciences Information Services", (Nov. 2001), "Nucleated red cell quantities and true graft cell dose in cord blood banking and transplantation: Critical influence on its detection by the counting method." Database accession no. PREV200200153215, XP–002214278, Abstract & Blood vol. 98. No. 11, Part 1, (Nov. 2001), 43rd Annual Meeting of the American Society of Hematology, Part 1, (Dec. 2001), pp. 181a—ISSN: 0006–4971.

Andrews et al., "Enrichment of Fetal Nucleated Cells from Maternal Blood: Model Test System Using Cord Blood", Prenatal Diagnosis, vol. 15, (1995), pp. 913–919.

Cranedonk et al., "Reference Values for Automated Cytochemical Differential Count of Leukocytes in Children 0–16 Years Old: Comparison with Manually Obtained Counts from Wright–Stained Smears", J. Clin. Chem. Clin. Biochem. vol. 23, (1985) pp. 663–667.

Gluckman et al., "Outcome of Cord–Blood Transplantation from Related and Unrelated Donors", New England Journal of Medicine, vol. 337, No. 6, (Aug. 1997), pp. 373–381.

Hanlon–Lundberg et al., "Nucleated Red Blood Cells in Cord Blood of Singleton Term Neonates", Am. J. Obstet. Cynecol., (Jun. 1997), pp. 1149–1156.

Kögler et al., "Hematopoietic Transplant Potential of Unrelated Cord Blood: Critical Issues", Journal of Hematotherapy (1996) pp. 105–116.

(List continued on next page.)

Primary Examiner—Leon B. Lankford, Jr.
(74) Attorney, Agent, or Firm—Paul T. Clark; Clark & Elbing LLP

(57) ABSTRACT

A method to determine an engrafting cell dose of hematopoietic stem cell transplant units from transplant sources having nucleated cells selected from the group consisting of cord blood, bone marrow, peripheral blood comprising the steps of subjecting the source to a substantially complete erythrocyte lysis, measuring in a cell counter a signal corresponding selectively to white blood cells, assessing essentially quantitatively nucleated red blood cell (NRBC) count as part of the total nucleated cell (NC) count, and determining the number of white blood cells (WBCs) as transplant relevant cells.

10 Claims, 10 Drawing Sheets

OTHER PUBLICATIONS

Kögler et al., *"Volume Reduction of Cord Blood by Hetastarch or Long–Term Stem Cell Banking"*, Bone Marrow Transplantation (1998) vol. 22 suppl. pp. S14–S15.

Nikischin et al., *"The Influence of Mode of Delivery on Hematologic Values in the Umbilical Vein"*, Gynecologic and Obstetric Investigation, Gynecol Obstet Invest. (1997), vol. 43, pp. 104–107.

Normal blood values in the newborn period. Hematolomic problems in the newborn. Philadelphia, USA, W.B. Saunders: pp. 1–21.

Serrani et al., *"States of stability/lysis in human fetal and adults red blood cells"*, Archives Internationales de Physiologie et de Biochimie, (1989), vol. 97, pp. 309–316.

Carlson et al., *"Placental–Blood Banking—A New Frontier in Transfusion Medicine"*, New England Journal of Medicine, (Jul. 1996), vol. 335. No. 3, pp. 199–201.

METHOD TO DETERMINE AN ENGRAFTING CELL DOSE OF HEMATOPOIETIC STEM CELL TRANSPLANT UNITS

This is a complete application claiming benefit of provisional No. 60/245,167 filed Nov. 3, 2000.

The invention pertains a method to determine cell dose of hematopoietic stem cell transplant units from transplant sources having nucleated cells.

BACKGROUND OF THE INVENTION

Transplantation of hematopoietic stem and progenitor cells from umbilical-cord blood (CB) can restore the function of bone marrow and sustain hematopoietic recovery in both related and unrelated recipients (Gluckman, et al. 1989; Kutzberg, et al. 1996). For patients for whom no suitable related donor is available, this source of hematopoietic stem cells offers substantial advantages, because of the relative ease of procurement; the absence of risk to the donor; the small likelihood of transmitting clinically important infectious diseases such as cytomegalovirus (CMV) and Epstein-Barr (EBV) virus infections; the rapid availability of placental blood to transplantation centres; and the low risk of severe graft-versus-host disease (GVHD) when compared to unrelated bone marrow transplantation (Gluckman, et al. 1997; Rubinstein, et al. 1998). The reduced risk and severity of GVHD permits the use of transplants from HLA-mismatched CBs and improves the likelihood of finding transplant units for patients with uncommon tissue types. For these reasons, worldwide cord-blood banks have increased the use of cord-blood transplantation in patients with hematologic disorders (Silberstein, et al. 1996).

Large retrospective studies of the performed bone marrow transplantations until 1998 with more than 600 evaluable cases have shown that the number of nucleated cells infused per kilogram was a major factor predicting the recovery to clinically relevant neutrophil and platelet counts. The leukocyte content of the graft relates principally to the speed and overall success of engraftment and secondarily to transplantation-related events and event-free survival. Consequently, doses of leukocytes from larger placental-blood collections may improve event-free survival, particularly for older patients (Gluckman, et al. 1997; Rubinstein et al. 1998). For these reasons, the success of cord blood transplants critically depends on the correct determination of the white blood cells WBC counts in CB transplantation units.

It is well established with new-born patients that nucleated red blood cells (NRBC) and lysis resistant red cells are negatively influencing the quality of automated WBC determination in cord blood samples (Cranendonk, et al. 1985; Johannessen, et al. 1990; Hanion, et al. 1997; Walka, et al. 1998).

Analysis of neonatal or cord blood samples has always been different than adult blood samples (Johannessen, et al. 1990). Interpretation of the automated (WBC) count results can be problematical because of the marked alterations in reference limits during the first hours of life (Johannessen, et al. 1990). Newborn blood samples often contain remarkable number of normoblasts sometimes even exceeding WBC counts, which are counted by all haematological analysers based on the Coulter principle as WBCs, namely lymphocytes (Nikischin, et al. 1997; Oski, et al. 1966; Dörner, et al. 1995; Lim, 1994). Further, subpopulations of neonatal red blood cells (RBC) have a higher osmotic resistance than normal adult RBCs (Serrani, et al. 1989).

SUMMARY OF THE INVENTION

Cord Blood (CB) transplantation for allogeneic bone marrow reconstitution is used with increasing success similar to other stem cell sources. The speed of engraftment in allogeneic transplantation is strongly associated with the graft cell dose. Therefore the quality control of cord blood regarding the content of the true progenitor cell number is of great importance for CB banking and transplantation.

In most cord blood banks, also in Bone Marrow transplantation and peripheral blood stem cell centers, the cell number used for transplant unit description is derived from nucleated cells (NCs) including nucleated red blood cells (NRBCs). In cord blood transplants the NRBCs can reliably be counted only on a manual basis (smear differential).

It is therefore an object of the invention to provide a reliable method for accurately assessing cord blood transplant as well as bone marrow and, apheresis products, true white blood cells based on cell counts.

It is another object of the invention to provide a method which can be performed substantially automatically.

The present invention provides a method to determine an engrafting cell dose of hematopoietic stem cell transplant units from transplant sources having nucleated cells selected from the group consisting of cord blood, bone marrow, peripheral blood comprising the steps of subjecting the source to a substantially complete erythrocyte lysis, measuring in a cell counter a signal corresponding selectively to white blood cells (WBCs), assessing essentially quantitatively nucleated red blood cell (NRBC) count as part of the total nucleated cell (NC) count, and determining the number of white blood cells (WBCs) as transplant relevant cells.

Blood samples from new-borns frequently contain a remarkable concentration of normoblasts, which sometimes are even exceeding the white blood cell (WBC) concentration. To determine the real graft cell dose as white blood cells without erythroblasts the content of nucleated red blood cells (NRBC) was determined. The difference of nucleated cell (NC) count and white blood cell (WBC) count regarding the concentration of nucleated red blood cells (NRBC) was not taken into account when the success of CB transplantations were assessed in the past. Measuring the nucleated cell count only by an impedance counting method systematically overestimates the white cell dose in these cryopreserved CB transplant units. Therefore the graft cell dose in Cord Blood Banking should always be corrected for the actual quantity of nucleated red cells in each CB preparation. Because of the selection of CB units by the transplant centers on the number of nucleated cells in correlation to the body weight of the individual patient, this number should always be documented in the inventory of each cord blood bank to be available for the transplant center prior to the selection of a CB transplant unit.

The present inventions uses the impact of different cell counting methods on the determination of the transplant cell dose for CB grafts.

DETAILED DESCRIPTION OF THE INVENTION

Figure 1:
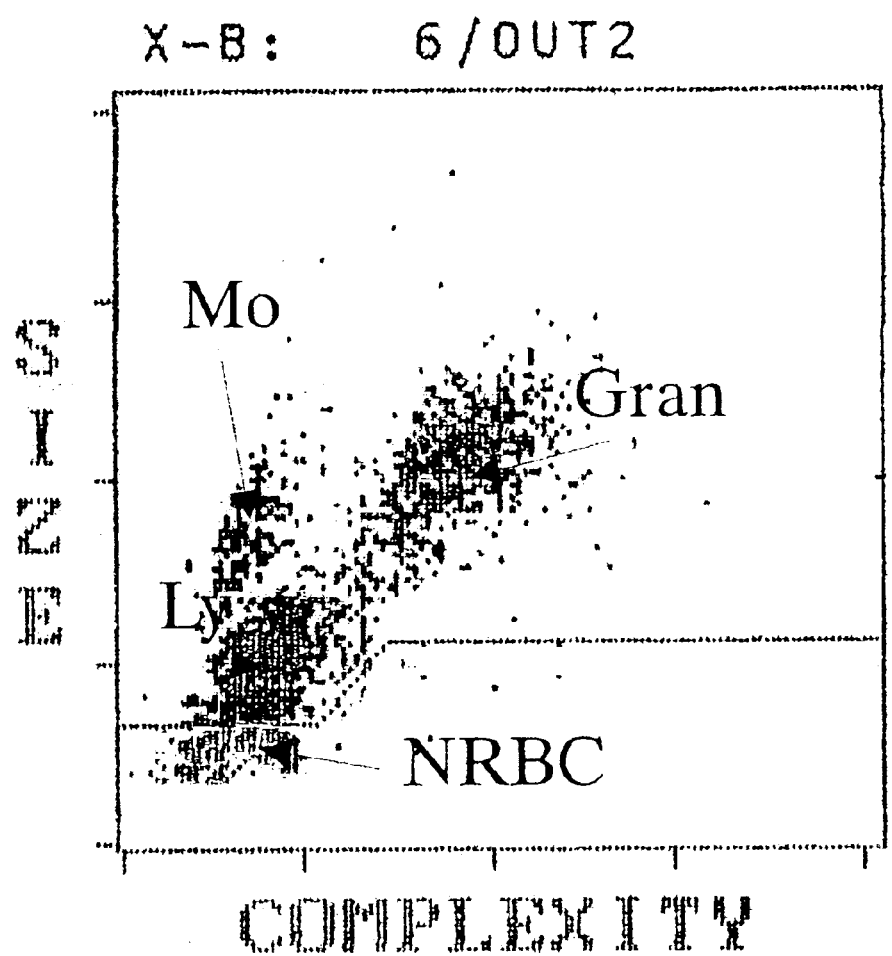
FIG. 1: Scatterplot of a typical CB sample of the CD3500. The sample was measured in extended lysis mode. NRBC Cluster is marked and gated out by dynamic thresholding of the instrument.

According to a preferred embodiment of the invention the substantially complete lysis is achieved by treating a sample of the transplant source for a sufficient time longer than standard erythrocyte hypotonic conditions (extended hypotony). This leads to lysis of erythrocytes before the cell count is achieved, especially to lysis of normally lysis resistant cells.

Hypotony is a state of low osmotic pressure for example surrounding the cells which leads to osmotic shock and destruction of the NRBC.

In particular, the signal corresponding to white blood cells (WBC—signal) is generated by an optical measurement of the sample.

This embodiment allows differentiation of NRBC from WBC.

In another embodiment of the invention the nucleated cells in the sample are enriched (e.g. due to manufacturing process) before subjecting the sample to an extended hypotony.

It may be advantageous to enrich the sample for example by density gradient centrifugation to yield an enriched fraction of the cells suitable to transplantation.

If an enrichment was performed, it may be necessary to dilute the sample again, in particular when methods for enrichment were used which increases viscosity of the sample or fraction.

As control, additionally the impedance count of the sample can be measured to determine the exact number of NRBCs.

Nucleated red blood cells (NRBC) are separated by a cell separator, preferably a cell counter for example the Cell-DYN 3500™ device (Abbott Diagnostics GmbH, Wiesbaden-Delkheim). The separation may advantageously be performed automatically in an optical measurement chamber from lymphocytes using a floating threshold as disclosed by Dörner, K., et al. (1995). "Improved automated leucocyte counting and differential in newborns achieved by the haematology analyser CELL-DYN 3500 [see comments]." Clin-Lab-Haematol 17(1): 23–30 and Walka, M. M., et al. (1998). "Complete blood counts from umbilical cords of healthy term newborns by two automated cytometers." Acta Haematol 100(4): 167–73, the disclosure is incorporated by reference. While using an extended lysis mode, lysis resistant red blood cells are destroyed and therefore cannot influence the cell count in the optical channel of the CD3500 unit (Dörner, et al. 1995). Simultaneously these NRBCs and other leukocytes are preferably detected together in the impedance channel of the CeliDyn 3500™ device (Dörner, et al. 1995). Therefore subtracting the optical count from the impedance count gives the correct number of NRBCs, as proven with manual differential counts (Walka, et al. 1998; Dörner, et al. 1995).

More than 2000 Cord Blood Units were analyzed. In these samples the number of nucleated cells was higher than previously described based on small blood draws of the newborn part of the cord (12.2 NRBCs per 100 WBC (Q5–95% 2.06 to 26.2). (Hanion Lundberg, et al. 1997).

As found by other investigators (Andrews, et al. 1995), further volume reduction through sedimentation results in an enrichment of NRBCS (18.1 per 100 WBC (Q5–95% 9.05 to 36.5) (Andrews, et al. 1995). This enrichment can reach values up to 21.7 fold through the volume reduction process (median 1.44). While most of the NRBCs are lysed through the freezing thawing procedure, a poor recovery of NCs is seen, if only the NC count is taken into account—especially in units with high NRBC content or after volume reduction with high enrichment of erythroblasts.

In contrast, nearly all MNCs could be recovered after the freezing thawing procedure, using the optical counts as basis for yield calculation. Thus taking the nucleated cell count before volume reduction as decision point for transplant selection will lead to an overestimation of the graft cell dose.

Taken this together a better estimator for the effective graft cell dose is the number of white blood cells without NRBCS after processing, before freezing than the collected nucleated cell number including those erythroblasts before volume reduction. For the fully automated determination of the graft cell dose impedance only based systems are not suitable.

The invention is further described by the non-limiting examples.

EXAMPLES

Methods

2192 CB units were collected analyzed and cryopreserved at the NETCORD Bank Germany, Düsseldorf. Every CB specimen was processed within 36 hours after delivery, including primary quality control such as cell counts. Cells were primarily collected using ACDA as anticoagulant either with the placenta in utero in vaginal delivery or with the placenta ex utero after section by puncture of the umbilical vein after clamping (Kögler, et al. 1996).

1464 of those 2192 units were volume reduced prior to cryopreservation. Volume reduction was performed according to the protocol of P. Rubinstein et al. applying Hetastarch sedimentation (Rubinstein, et al. 1995) with the modification that extended aliquots for routine testing were prepared as described (Kögler, et al. 1998).

728 CB units were cryopreserved as whole blood as described (Kögler, et al. 1996).

Cell number was determined on all CB units before processing. In addition, cell counts were determined for volume reduced units before addition of the cryoprotectant.

In all samples the complete blood cell count was determined on a CELLDYN 3500 (Abbott Diagnostics GmbH, Wiesbaden-Delkheim) (CD3500) running Software version 1.35.

The CD3500 uses two different channels for WBC counting: a WBC optical channel (WOC), which includes hydrodynamic focusing of diluted blood and laser optical measurement of WBC and their light scatter properties, and an impedance channel (WIC), which utilizes the classical impedance (Coulter) principle to count NC.

The WOC channel is used for counting of the cells and creating a differential, whereas the WIC (impedance) channel is used as a confirmation channel by enumerating cells and determining their volume. The lytic reagent used in the WIC channel is based on detergents and is more aggressive against RBC than that of the WOC channel, which is hypotonic and leucoprotective. A 15 seconds extension of the red cell lysis time for measurement for the WOC channel—eliminates lysis resistant red blood cells, which are common in newborn blood samples—effectively (Dörner, et al. 1995). NRBC are detected in the WOC Channel with high sensitivity and are excluded from the WBC count by dynamic thresholding (Dörner, et al. 1995) (FIG. 1). Extended lysis can be provided by the device, if selected, so all samples were measured in extended lysis mode.

33 samples of the transplant units, which were frozen as whole blood were additionally counted manually with erythrocyte lysis and staining with Turk solution using a standard hemocytometer with 0.9 µl count volume as described previously (AABB 1996).

From 11 as whole blood frozen units a cryo-aliqout was thawed and counted immediately after thawing with the CD3500 and manually as described.

From 106 cryo-aliqouts of the units frozen as whole blood and from 115 units frozen after volume reduction differential counts were performed as described above and NC and MNC recovery was determined.

In 77 volume reduced CB units all cell counts were performed additionally to the CD3500 measurement with a Coulter ACT device (Beckmann/Coulter Diagnostics, Krefeld). The white blood cell count in the Coulter ACT performs the cell count within an impedance chamber, determining the volume of the nucleolus of the measured cell. The differential count of this device is based on the volume of the measured nucleoli: cells with low volume nucleoli are counted as lymphocytes, median as monocytes and cells with a high nucleolus volume as granulocytes.

The CD3500 and the ACT were operated continuously on a 12 h schedule. Internal and external quality control was performed in accordance with the regulations of the German Bundesärztekammer.

Statistical description data is given by arithmetic mean values ± standard deviations in normal distributed data and otherwise by median and Quantile (5%–95%).

Regression analyses were performed using a best fit model containing linear, potential, logarithmic, reciprocal correlation. Fop comparison of distributions, t-test or where indicated paired t-tests were used.

Results

A total of 2192 Cord blood units could be analyzed for volume, optical and impedance count on the CD3500. Mean volume of the collected CB was 98.3 ml ±21.2 ml containing 21 ml ACDA as anticoagulant.

Figure 2:
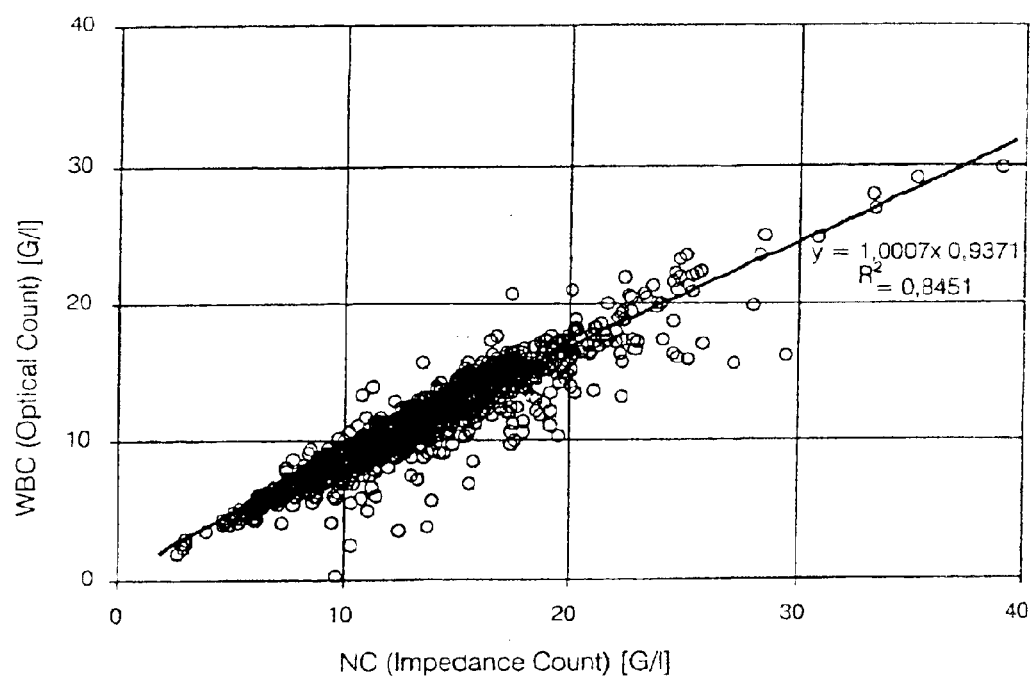
FIG. 2: Correlation of White Blood Cell (WBC) with Nucleated Cell count (NC) of unprocessed cord blood (n=2192) performed on a Cell Dyn 3500.
Figure 3:
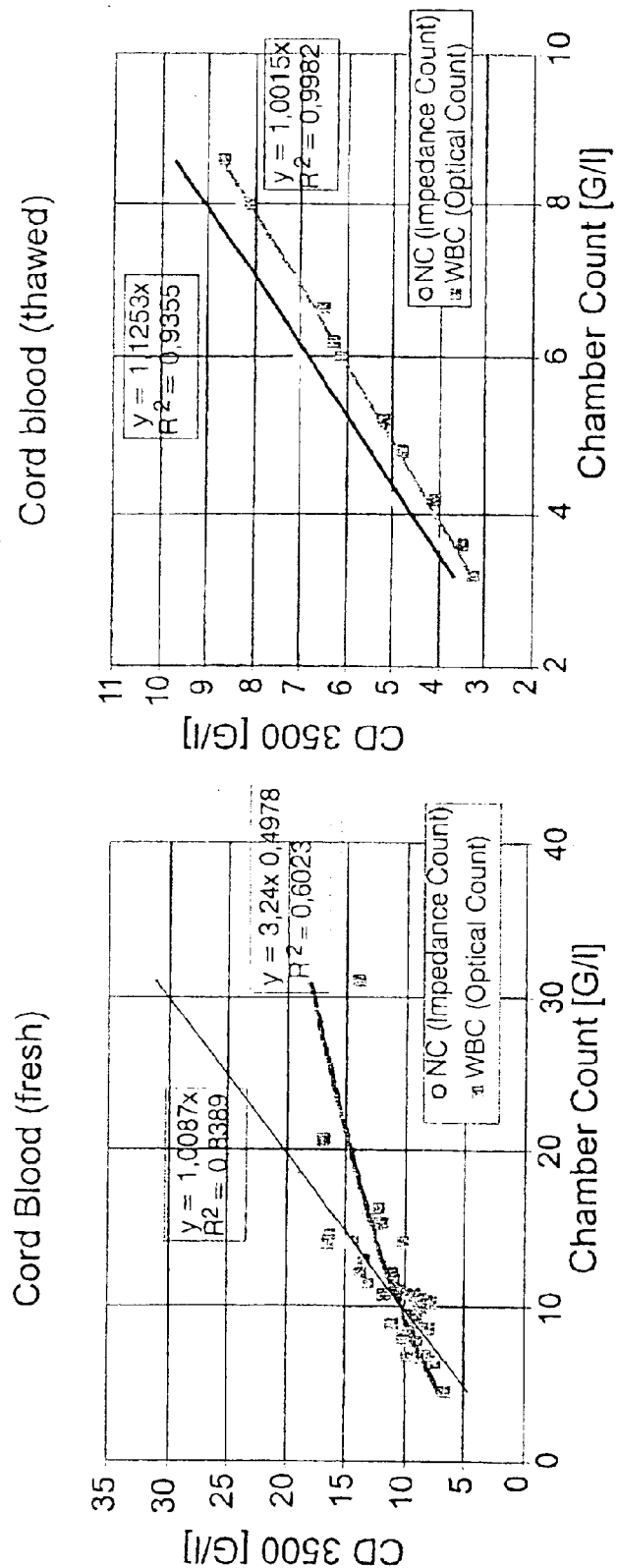
FIG. 3: Correlation of White Blood Cell Count determined on the Cell Dyn 3500 device with chamber count using Turks solution after red cell lysis in fresh (n=37) and thawed CB (n=10).

A mean of $10.69 \pm 3.30 \times 10^9$/l cells could be detected by the optical channel of the Abbott CD3500 in CB after collection before further processing. $12.5 \pm 4.1 \times 10^9$ nucleated cells/l were determined by the impedance channel of the system (Table 1). Best fit correlation the impedance count correlates well with the optical count ($r^2=0.8451$; $p<0,0001$). FIG. 2 shows the correlation of White Blood Cell (WBC) with Nucleated Cell count (NC) of unprocessed cord blood (n=2192) performed on a Cell Dyn 3500. The WBC count correlates with NC in a potential fashion in a best fit correlation model containing linear, logarithmic, potential and polynomial algorithm, indicating that in samples with high NC count there is a greater proportion of nucleated red blood cells than in samples with low NC concentrations, especially for samples with NC count >20 G/l. To prove which cells are measured in the optical and impedance channels, 33 unprocessed samples were measured by the CD 3500 device and by manual chamber count using crystal violet after lysing the red blood cells. A linear correlation was observed between the impedance and chamber count (WIC=1,009×chamber count, $r^2=0.8389$), indicating that the nucleated red blood cells are counted together with the white blood cells in the impedance channel as nucleated cells (NC). FIG. 3 shows the correlation of White Blood Cell Count determined on the Cell Dyn 3500 Device with chamber count using Turks solution after red cell lysing in fresh (n=37) and thawed CB (n=10). NC (impedance) count correlates in linear fashion with the chamber count in fresh and thawed samples, whereas the WBC (optical) count correlates with the chamber count in a potential manner in fresh samples, in linear fashion in thawed samples, indicating that through freezing/thawing most of the NRBC are destroyed.

In sharp contrast, the optical count (WOC) correlates with the chamber count with the curve below a 1:1 correlation, indicating that only WBCs are counted. The observed difference between WIC (NC) and WOC (WBC) count is caused by the NRBC content. Interestingly, CB units with high NC concentrations also can result in higher NRBC concentrations (FIGS. 2 and 3 left panel).

In thawed samples, both impedance and optical counts correlate in a linear fashion with the chamber count (WIC=1,125×chamber count, $r^2=0.936$; WOC=1.002×Chamber count $r^2=0.998$), indicating that most of the NRBCs are lysed through the freezing/thawing procedure (FIG. 3 right panel).

Of the 2192 samples, 1464 were volume reduced through Hetastarch volume reduction.

Figure 4:
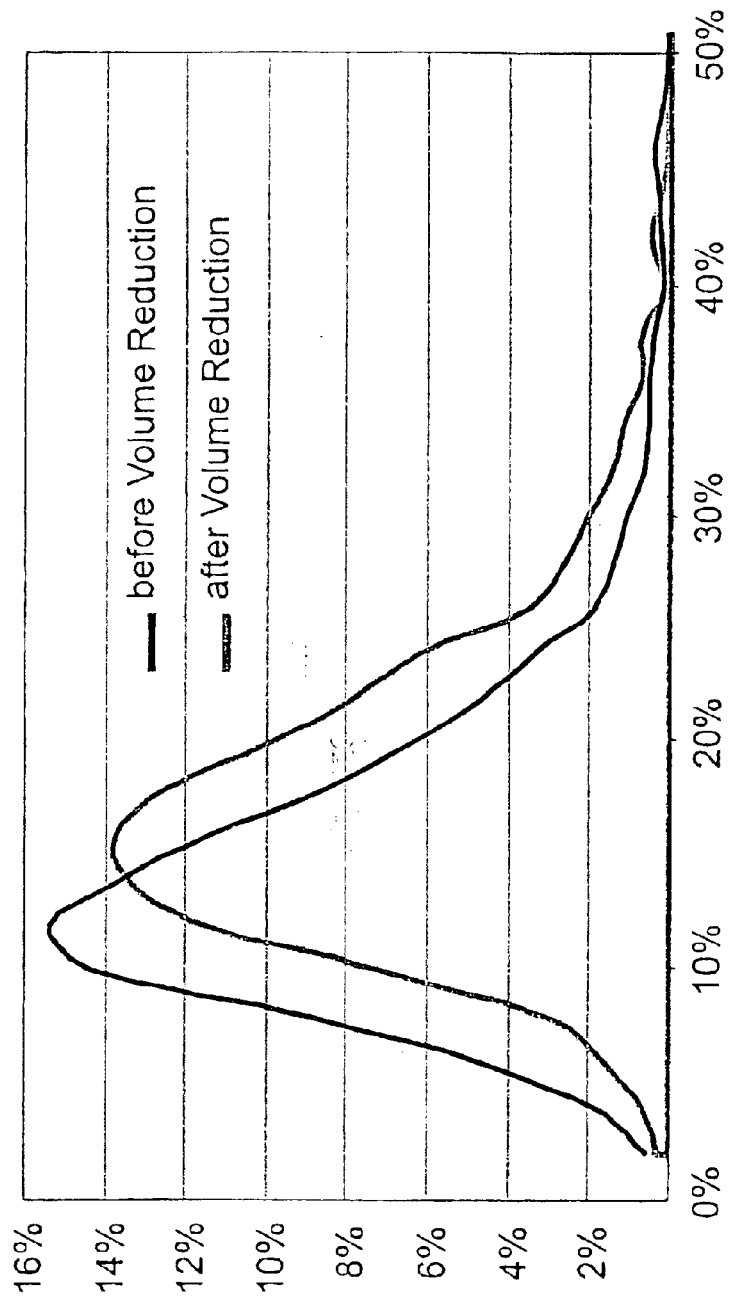
FIG. 4: Distribution of Nucleated Red Blood Cells (NRBC) in CB before and after Hetastarch (Hespan) Volume reduction.

From all the volume reduced units again WBC (WOC) and NC (WIC) count were determined on the CD3500. The percentage of NRBC of NC was calculated as 100×(1-WOC/WIC). After volume reduction more NRBCs could be found than in the samples before processing (p<0.00001). FIG. 4 shows the distribution of Nucleated Red Blood Cells (NRBC) in CB before and after Hespan volume reduction. NRBCs were determined as a NC count -WBC -count and calculated as percentage of NCs (n=1464). In volume reduced CBs a higher percentage of NRBC on NC is found than in unprocessed CB, indicating that Hetastarch (Hespan) volume reduction enriches NRBCs in CB. In whole CB a median 12.75% of the NCs are NRBCs (Q5–95% 5.41–26.73%, range 0.8%–75.1%), in CB after Hetastarch volume reduction, 15.98% (Q5–95% 7,89–29,72%, range 0,27–58,97%).

Figure 5:
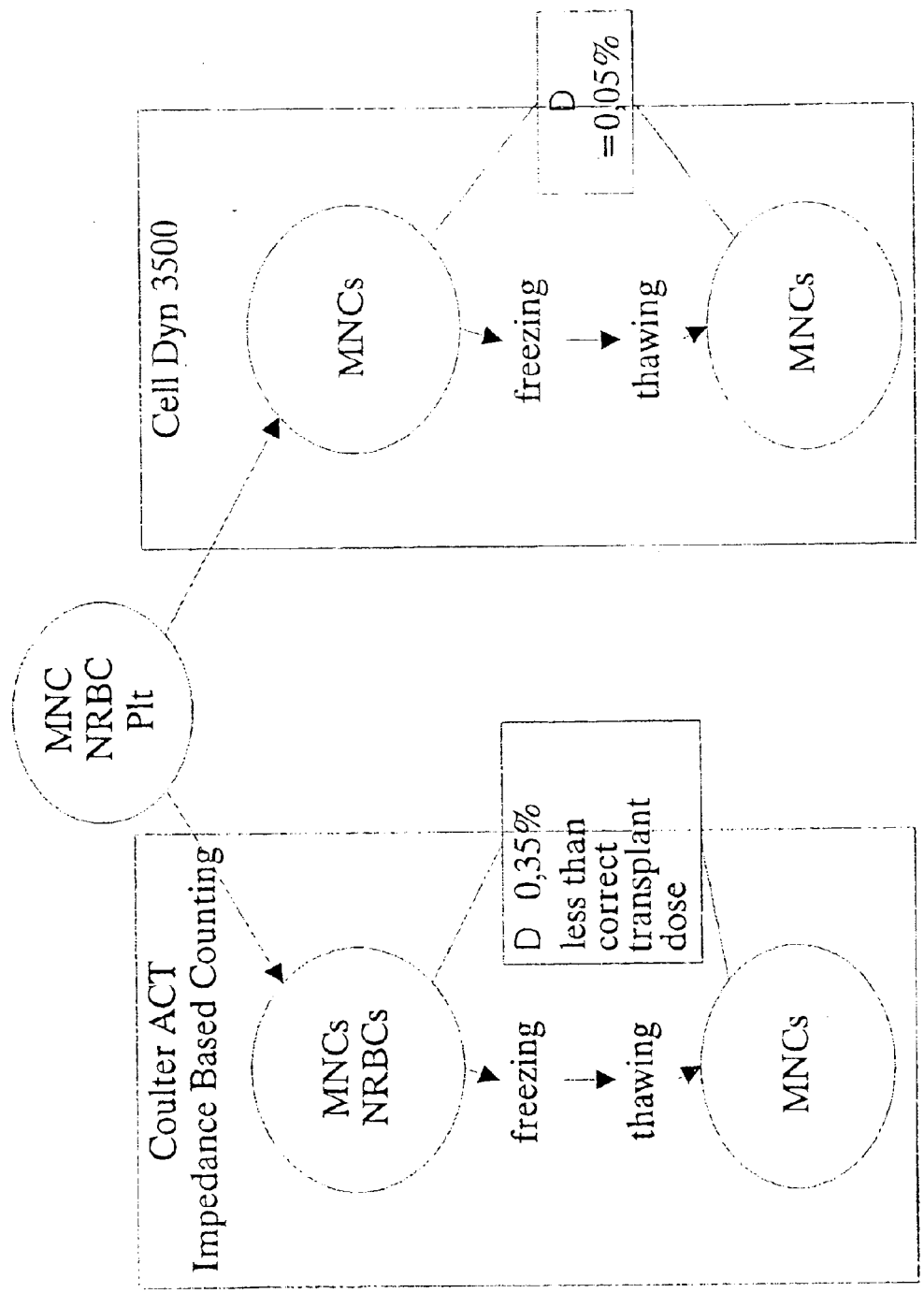
FIG. 5: Determintation of the Recovery of thawed CB-MNC cells by different counting methods. MNCs were determined by Coulter ACT resp. AbottCell Dyn 3500 device, recovery calculated as MNC before freezing, MNC after thawing.

In 106 thawed aliquots of CB units frozen as whole blood and in 115 aliquots of CBs frozen as volume reduced units 95.3%±7.2% and 92.3%±6.5% of the MNC could be recovered if MNC are determined by optical counting (WOC, cell count without NRBC). Only 65.2%±23.2% of the MNCs in units frozen as whole blood and 50,4%±8.1% of the MNCs in units frozen as volume reduced products could be recovered if the cells are counted and differentiated by impedance method. This suggests that the NRBCs are destroyed through the thawing/freezing procedure (FIG. 5).

Figure 6:
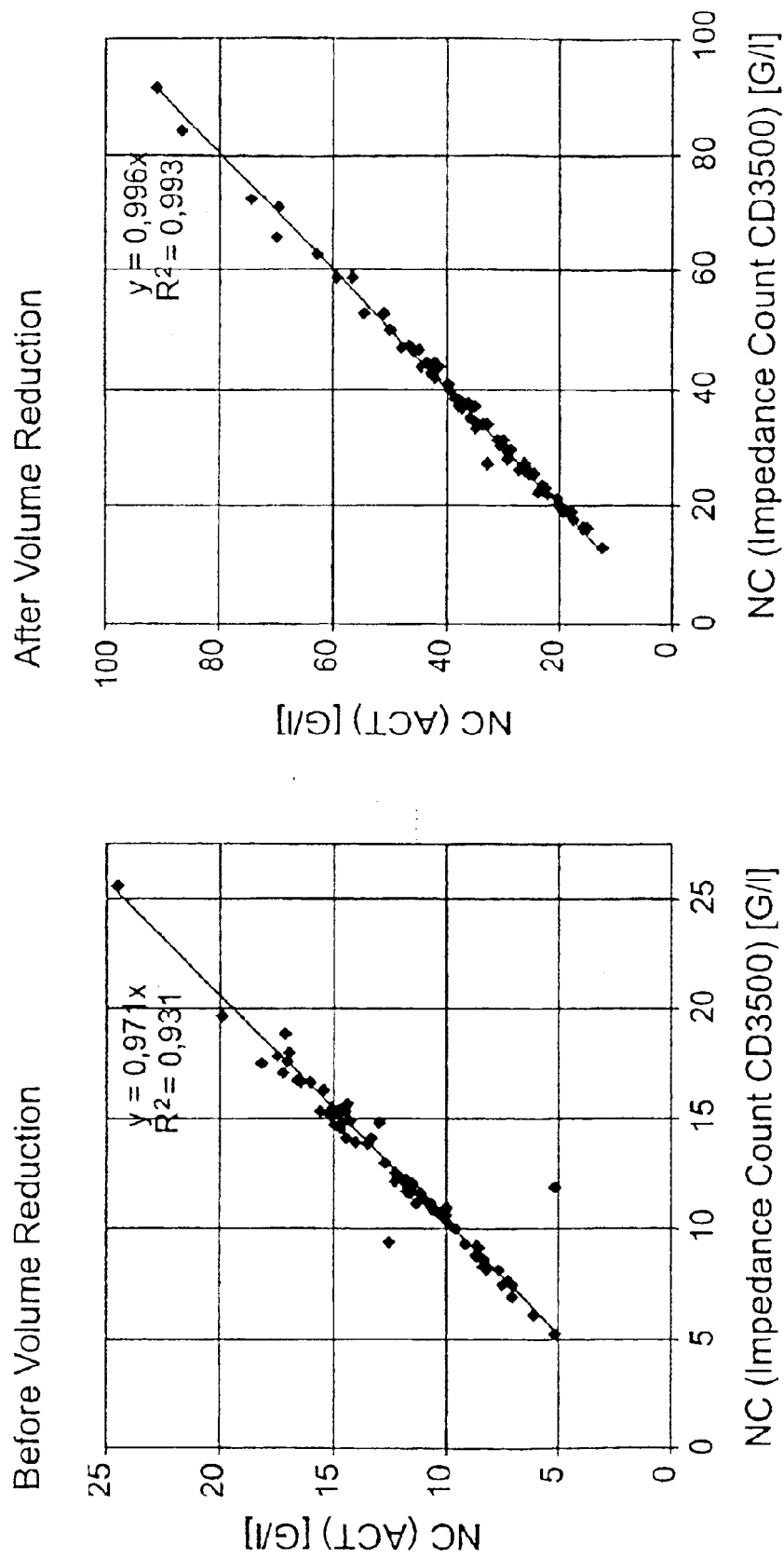
FIG. 6: Correlation of Nucleated Cell (NC) Count between the impedance based Cell Counter Coulter ACT and the impedance channel of the Cell Dyn 3500 in unprocessed and volume reduced cord blood.
Figure 7:
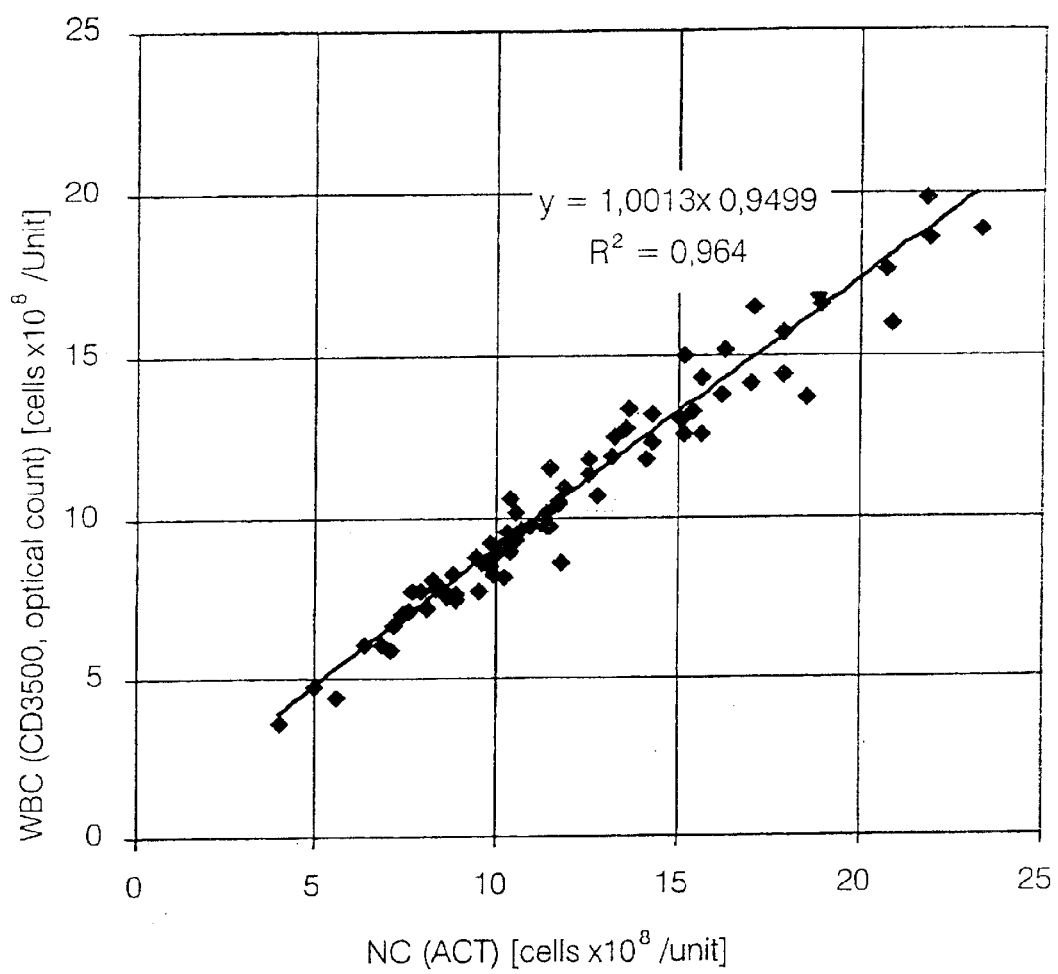
FIG. 7: Correlation of Graft Cell Dose determined by Abott CD3500 (optical measurement, WBC) and Coulter ACT (impedance count, NC).

As demonstrated by results obtained with 77 volume reduced units, very good linear correlation was detected between the impedance count of the CD3500 and the estimated NC count given from the ACT device in whole cord blood (NC(ACT)=0.971 WIC, $r^2$=0,931) and in the Hetastarch volume reduced unit (NC(ACT)=0,996×WIC, $r^2$=0,993), indicating that all NRBC counted by the impedance channel of the CD3500 are detected also by the ACT. FIG. 6 shows a correlation of Nucleated Cell (NC) Count between the impedance based Cell Counter Coulter ACT and the impedance channel of the Cell Dyn 3500 in unprocessed and volume reduced cord blood. Clear linear correlation is found between the impedance measurement of the Cell Dyn 3500 and the Coulter Device. Under the conditions of best fit, the total cell content determined by CD3500 of the whole unit before volume reduction correlates in a potential manner with the NC determined by the ACT ($r^2$=0.964) with the correlation curve being lower than an 1:1 correlation, as seen in the correlation between WIC and WOC channel and WOC channel and chamber count. FIG. 7 shows the correlation of Graft Cell Dose determined by Abbott CD3500 (optical measurement, WBC) and Coulter ACT (impedance count, NC). The WBC content of the graft determined by the Abott CD3500 correlates with the content determined by the ACT in a potential fashion in a best fit correlation model, indicating that in samples with high NC count there is a greater proportion of nucleated red blood cells than in samples with low NC concentrations. In particular in CB transplant units with high cell content the proportion of NRBCs is higher than in units with lower WBC counts. In the volume reduced product a potential correlation ($r^2$=0.965) is also seen (best fit model), with the graph being lower than a 1:1 relation, especially for grafts with high cell content.

Figure 8:
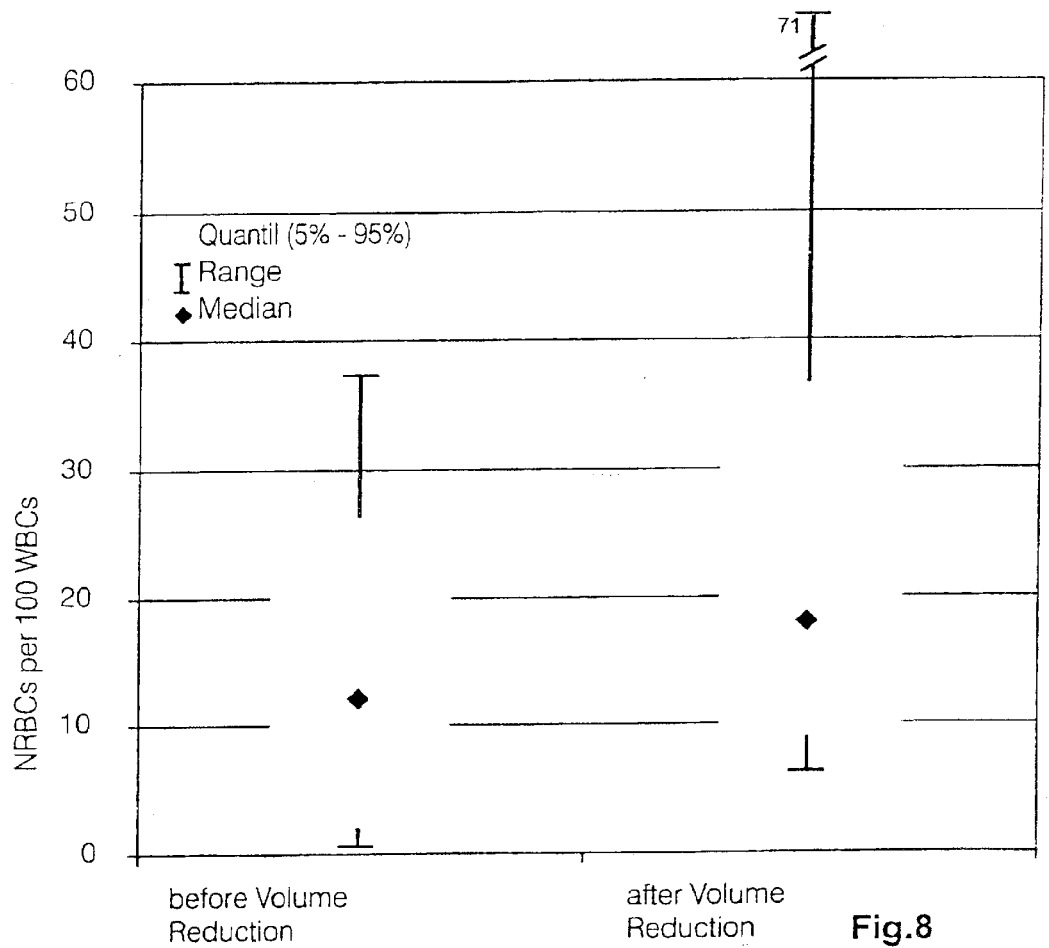
FIG. 8: NRBCs per 100 WBCs in CB before and after Hetastarch (Hespan) volume reduction.

Through Hetastarch volume reduction the number of NRBCs per 100 WBC is increased from median 12.2 ($Q_{5-95\%}$ 2.06 to 26.2, range 0.5–37) to 18.1 ($Q_{5-95\%}$ 9.05 to 36.5, range 6.9–71.0). FIG. 8 shows NRBCs per 100 WBCs in CB before and after Hetastarch volume reduction. NRBCs were determined as a NC generated from Coulter ACT and WBC determined by Cell Dyn 3500 (optical count) running under extended lysis mode. After volume reduction a higher Number of NRBCs can be found than before volume reduction (n=77).

Figure 9:
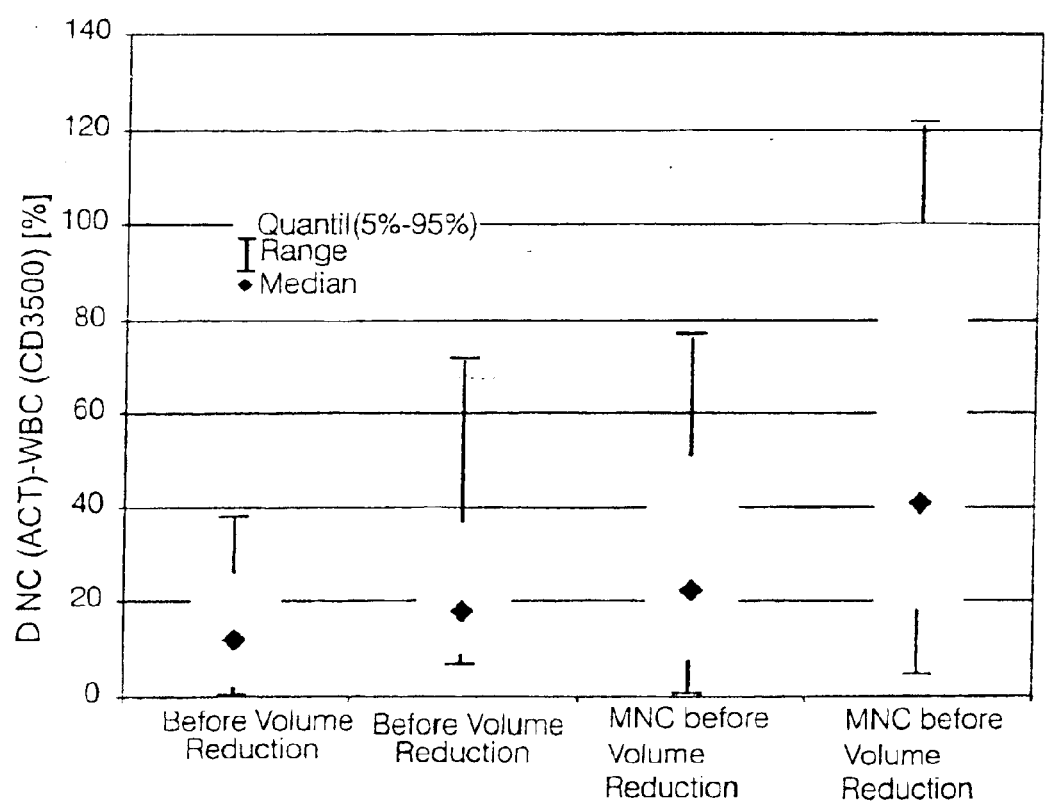
FIG. 9: Comparison of WBC and MNC count using the Coulter ACT and the Abott Cell Dyn 3500 Device in CB Quality Control.

FIG. 9 shows the comparison of WBC and MNC count using the Coulter ACT and the Abott Cell Dyn 3500 Device in CB Quality Control.

Plotted are the differences between the obtained results from the Coulter ACT and the Cell Dyn 3500, using extended lysis and optical count, before and after volume reduction regarding to WBC and MNC count. The differences are related to the count of the Abbott device (n=77). Counted by the Coulter ACT, the median number of MNCs is 22.2% higher than using the CD3500 for the differential count method (range 0.5% to 75.7%, $Q_{5-95\%}$ 7.5 to 50.8%) (FIG. 9). This difference was even higher after volume reduction, with up to 120.7% higher values for MNC counted with the ACT than counted with the CD3500 in the optical channel (median 40.6%, range 4.4% to 120.7%, $Q_{5-95\%}$ 18.6 to 100.0%) (FIG. 9).

Thus taking the nucleated cell count obtained by impedance counting methods systematically overestimates the white cell dose of these CB grafts. Therefore the graft cell dose in Cord Blood Banking should be corrected for the actual quantity of nucleated red cells which should be documented in the banks inventory as well as reported to the transplant center.

Figure 10:
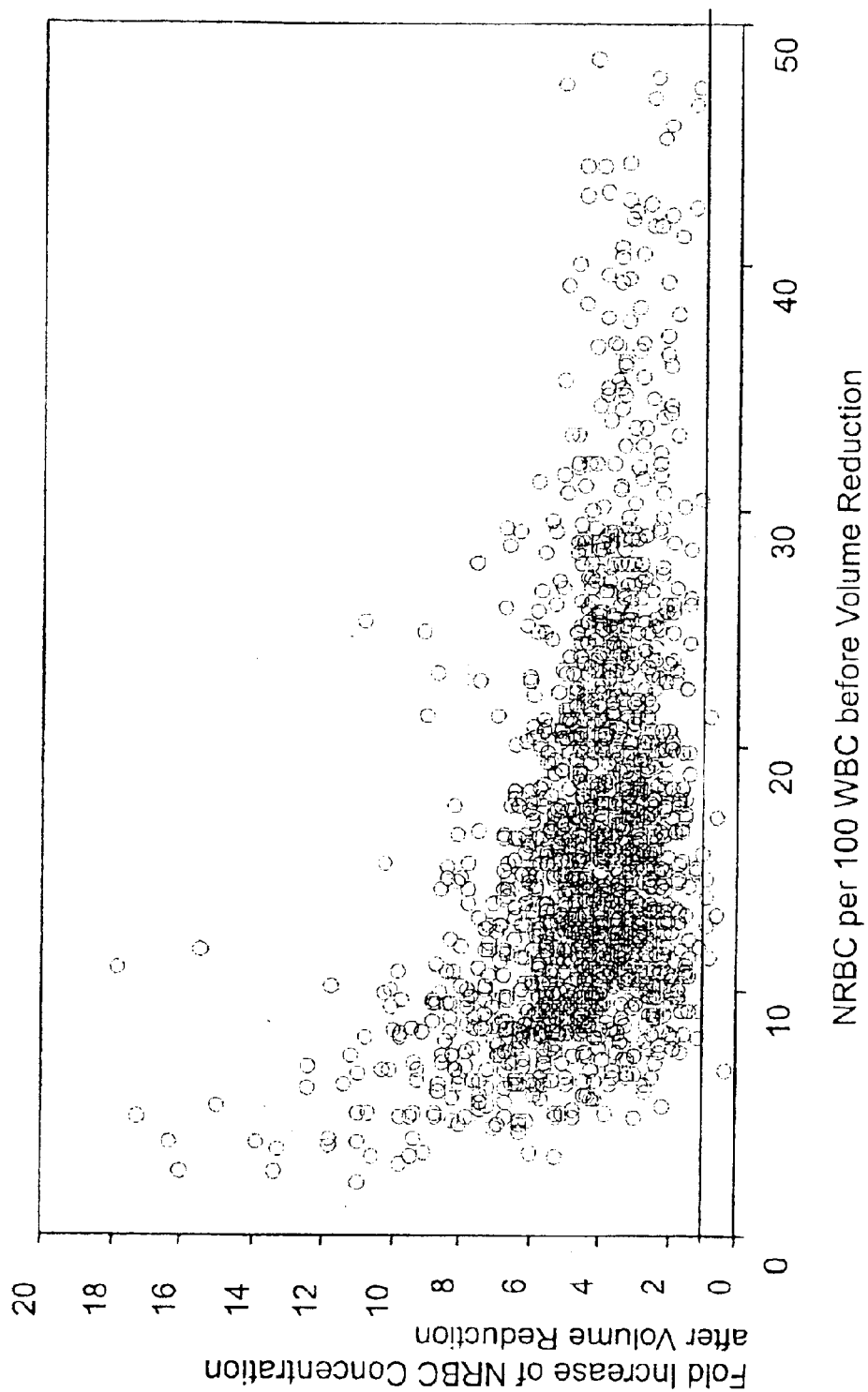
FIG. 10: Fold Increase of NRBC by Hetastarch Volume Reduction of CB.

FIG. 10 shows fold Increase of NRBC by Hetastarch Volume Reduction of CB. Fold increase of NRBC was calculated through NRBC concentration before/NRBC concentration after volume reduction (n=1464).

Given the impedance count of the CD3500 as NC count including NRBC and the optical count of the CD3500 as WBC count without NRBC, NRBCs are enriched 1.44±1.21 fold (range 0.12 to 21.7 fold) through the Hetastarch volume reduction procedure (FIG. 10). In 76.4% of the 1464 volume reduction procedures, an enrichment of NRBC could be detected. In 11.4% of these volume-reduced units, a more than two-fold increase of the relative NRBC content was observed.

The NRBC content in CB, bone marrow grafts and apheresis units can readily be detected by the Cell Dyn 3500 device, proven by manual counting of NRBCs in white blood cell differential after May Grunwald staining. Whereas the method applied by Cell Dyn 4000 device gives correct numbers of NRBCs in bone marrow and apheresis grafts, the Cell Dyn 4000 device was not able to determine the correct number of NRBCs in CB transplant units.

TABLE 1

Nucleated Cell (NC) and White Blood Cell (WBC) Counts in CB before and after Hetastarch (Hespan) volume reduction

|  | Unprocessed | Volume Reduced |
| --- | --- | --- |
| WBC (optical measurement) [G/l] | 10.9 ± 3.6 | 35.1 ± 16.0 |
| MNC [G/l] | 4.4 ± 1.4 | 13.7 ± 5.8 |
| NC (impedance count) [G/l] | 12.5 ± 4.1 | 41.7 ± 19.0 |
| n | 2192 | 1464 |
| Volume before processing (including ACDA) [ml] | 98.3 ± 21.23 | 97.67 ± 21.18 |
| Volume after processing [ml] |  | 21–24 |
| # of bags cryoconserved per Unit | 1.71 ± 0.78 | 1.69 ± 0.78 |
| male | 1098 | 773 |
| female | 1004 | 691 |
| Vaginal delivery | 2041 | 1368 |
| Section | 151 | 96 |

Cell counts were performed on a Cell Dyn 3500. WBC was determined by optical measurement using extended lysis mode, NC by using the value of the impedance channel.

728 of the 2192 CB units were cryoconserved without any further volume reduction. (Volume after processing 91.1±21.3; stored in 1.71±0.78 bags).

Literature

AABB (1996). Counting residual white blood cells in leukocyte-reduced red cell concentrates. *Technical Manual*. V. Vengelen-Tyler. Bethesda, Md., USA, AABB: 722–724. Andrews, K., J. Wienberg, et al. (1995). "Enrichment of fetal nucleated cells from maternal blood: model test system using cord blood." *Prenat-Diagn* 15(10): 913–9.

Cranendonk, E., A. H. Geniip van, et al. (1985). "Reference values for automated cytochemical differential count of leukocytes in children 0–16 years old: Comparison with manually obtained counts from Wright-stained smears." *Journal Clinical Chemistry and Clinical Biochemistry* 23: 663–667.

Dömer, K., S. Schulze, et al. (1995). "Improved automated leucocyte counting and differential in newborns achieved by the haematology analyser CELL-DYN 3500 [see comments]." *Clin-Lab-Haematol* 17(I): 23–30.

Gluckman, E., H. E. Broxmeyer, et al. (1989). "Hematopoietic reconstitution in a patient with Fanconi's anemia by means of umbilical-cord blood from an HLA-identical sibling." *N Eng J* Med 321: 1174–1178.

Gluckman, E., R. Vanderson, et al. (1997). "Outcome of cord-blood Transplantation from related and unrelated donors." *N Eng J Med* 337: 373–381.

Hanion Lundberg, K. M., R. S. Kirby, et al. (1997). "Nucleated red blood cells in cord blood of singleton term neonates." *Am-J-Obstet-Gynecol* 176(6): 1149–54; discussion 1154–6.

Johannessen, B., T. Ommundsen, et al. (1990). "Automated differential leukocyte counts in newborn infants. Comparison of Coulter VCS and Technicon H1 with manual counts." *Eur J Haematol Suppl* 53: 41–4.

Kögler, G., J. Callejas, et al. (1996). "Hematopoietic transplant Potential of unrelated cord blood: Critical issues." *J. Hematotherapy* 5: 105–116.

Kögler, G., A. Samowski, et al. (1998). "Volume reduction of cord blood by Hetastarch for long-term stem cell banking." *Bone Marrow Transplant* 22(I): S14–5.

Kurtzberg, J., M. Laughlin, et al. (1996). "Placental blood as a source of hematopoietic stem cells for Transplantation into unrelated recipients." *N Engl J Med* 335-157–166.

Lim, F. T., L. van Winsen, et al. (1994). "Influence of delivery on numbers of leukocytes, leukocyte subpopulations, and hematopoietic progenitor cells in human umbilical cord blood." *Blood Cells* 20(2–3): 547–58.

Nikischin, W., M. Peter, et al. (1997). "The influence of mode of delivery on hematologic values in the umbilical vein." *Gynecol Obstet Invest* 43(2): 104–7.

Oski, F. A. and L. J. Naimann (1966), Normal blood values in the newborn period. *Hematolomic problems in the newborn*. Philadelphia, USA, W. B: Saunders: 11–21.

Rubinstein, P., C. Carrier, et al. (1998). "Outcomes among 562 recipients of placental-blood transplants from unrelated donors [see comments]." *N-Engl-J-Med* 339(22): 1565–77.

Rubinstein, P., L. Dobrila, et al. (1995). "Processing and cryopreservation of placental/umbilical cord blood for unrelated bone marrow reconstitution." *Proc-Natl-Acad-Sci-USA* 92(22): 10119–22.

Serrani, R. E., D. Alonso, et al. (1989). "States of stability lysis in human fetal and adults red blood cells." *Archives Internationales de Physiologie et de Biochemie* 97: 309–316.

Silberstein, L. E. and L. C. Jefferies (1 996). "Placental-blood banking-a new frontier in Transfusion medicine." *N Engl J Med* 335: 199–201.

Walka, M. M., J. Sonntag, et al. (1998). "Complete blood counts from umbilical cords of healthy term newborns by two automated cytometers." *Acta Haematol* 100(4): 167–73.

What is claimed is:

1. A method to determine the white blood cell content of an engrafting cell dose of hematopoietic stem cell transplant units from transplant sources having nucleated cells selected from the group consisting of cord blood, bone marrow, and peripheral blood comprising steps of:

enriching the nucleated cells, subjecting the source to a substantially complete erythrocyte lysis, diluting the enriched sample, measuring in a cell counter a signal corresponding selectively to the blood cells, measuring simultaneously in another device a signal corresponding electively to the number of cell nuclei as nucleated cell count, assessing essentially quantitatively nucleated red blood cell count part of the total nucleated cell count, and determining the number of white blood cells as transplant relevant cells.

2. The method according to claim 1, wherein the complete lysis is achieved by treating a sample of the transplant source for fifteen seconds longer than standard erythrocyte hypotonic conditions.

3. The method according to claim 1, wherein the signal corresponding to white blood cells is generated by an optical measurement of the sample.

4. The method according to claim 2, wherein the signal corresponding to white blood cells is generated by an optical measurement of the sample.

5. The method according to claim 1, wherein the sample is enriched density gradient centrifugation to yield an enriched, volume-reduced fraction.

6. The method according to claim 1, wherein additionally the impedance count is measured in the sample.

7. The method according to claim 2, wherein additionally the impedance count is measured in the sample.

8. The method according to claim 3, wherein additionally the impedance count is measured in the sample.

9. The method according to claim 4, wherein additionally the impedance count is measured in the sample.

10. The method according to claim 5, wherein additionally the impedance count is measured in the sample.

* * * * *

UNITED STATES PATENT AND TRADEMARK OFFICE
CERTIFICATE OF CORRECTION

PATENT NO. : 6,852,534 B2
DATED : February 8, 2005
INVENTOR(S) : Wernet et al.

It is certified that error appears in the above-identified patent and that said Letters Patent is hereby corrected as shown below:

Column 10,
Line 16, replace "to the blood cells" with -- to white blood cells --; and
Line 18, replace "electively" with -- selectively --.

Signed and Sealed this

Twenty-fourth Day of May, 2005

JON W. DUDAS
*Director of the United States Patent and Trademark Office*